United States Patent [19]

Wollweber et al.

[11] Patent Number: 4,957,919
[45] Date of Patent: Sep. 18, 1990

[54] 1-AMINOMETHYL-3-ARYL-4-CYANO-PYRROLES AND USE AS FUNGICIDES

[75] Inventors: Detlef Wollweber, Wuppertal; Wolfgang Krämer, Burscheid; Wilhelm Brandes, Leichlingen; Stefan Dutzmann, Duesseldorf; Gerd Hänssler, Leverkusen, all of Fed. Rep. of Germany

[73] Assignee: Bayer Aktiengesellschaft, Leverkusen, Fed. Rep. of Germany

[21] Appl. No.: 464,463

[22] Filed: Jan. 12, 1990

Related U.S. Application Data

[62] Division of Ser. No. 363,015, Jun. 8, 1989, Pat. No. 4,923,883, which is a division of Ser. No. 147,466, Jan. 25, 1988, Pat. No. 4,914,122.

[30] Foreign Application Priority Data

Jan. 31, 1987 [DE] Fed. Rep. of Germany ....... 3702852

[51] Int. Cl.$^5$ ............ A61K 31/38; A61K 31/40; C07D 417/12; C07D 413/12
[52] U.S. Cl. ............ 514/237.2; 514/227.8; 544/60; 544/141
[58] Field of Search ............ 544/60, 141; 514/227.8, 514/237.2

Primary Examiner—John M. Ford
Assistant Examiner—J. Richter
Attorney, Agent, or Firm—Sprung Horn Kramer & Woods

[57] ABSTRACT

Fungicidally active novel 1-aminomethyl-3-aryl-4-cyano-pyrroles of the formula

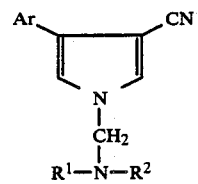

in which
Ar represents optionally substituted phenyl,
$R^1$ represents optionally substituted alkyl, represents alkenyl, alkynyl or cycloalkyl, or represents in each case optionally substituted aralkyl or aryl, and
$R^2$ represents in each case optionally substituted heterocyclylalkyl, heterocyclylalkenyl, heterocyclylalkynyl or heterocyclyl, represents dialkylaminoalkyl, or represents in each case optionally substituted cycloalkylalkyl or phenethyl.

11 Claims, No Drawings

1-AMINOMETHYL-3-ARYL-4-CYANO-PYRROLES AND USE AS FUNGICIDES

This is a division of application Ser. No. 363,015 filed June 8, 1989 now U.S. Pat. No. 4,923,883 which is a division of application Ser. No. 147,466 filed Jan. 25, 1988 now U.S. Pat. No. 4,914,122.

The invention relates to new 1-aminomethyl-3aryl-4-cyano-pyrroles, several processes for their preparation, and their use as pesticides.

It is already known that certain dithio-carbamates, such as, for example, zinc ethylene-1,2-bis-(dithiocarbamate) or manganese ethylene-1,2-bis-(dithiocarbamate), have good fungicidal properties (cf., for example, K. H. Büchel, "Pflanzenschutz und Schädlingsbekämpfung" (Plant protection and combating of pests), p. 137, 138, Thieme Verlag, Stuttgart 1977). It is furthermore known that certain sulphenamides, such as, for example, N,N-dimethyl-N'-phenyl-N'-(fluorodichloromethylsulphenyl)-sulphamide, have an excellent action, in particular against Botrytis species (cf., for example, K. H. Büchel "Pflanzenschutz und Schädlingsbekämpfung" (Plant protection and combating of pests), p. 141, Thieme Verlag Stuttgart 1977).

However, the activity of these previously known compounds is not completely satisfactory in all areas of application, in particular at low application rates and concentrations.

It is furthermore known that certain 3-aryl-pyrroles, such as, for example, 4-cyano-3-(2,3-dichlorophenyl)-pyrrole, likewise have good fungicidal properties (cf., for example, EP No. 174,910 or EP No. 182,738 or EP No. 133,247).

New 1-aminomethyl-3-aryl-4-cyano-pyrroles of the general formula (I)

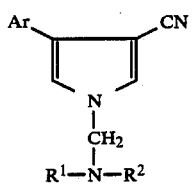

in which
Ar represents optionally substituted phenyl,
$R^1$ represents optionally substituted alkyl, represents alkenyl, alkynyl or cycloalkyl, or represents in each case optionally substituted aralkyl or aryl, and represents in each case optionally substituted heterocyclylalkyl, heterocyclylalkenyl, heterocyclylalkynyl or heterocyclyl, represents dialkylaminoalkyl or represents in each case optionally substituted cycloalkylalkyl or phenethyl, have been found.

It has furthermore been found that the new 1-aminomethyl-3-aryl-4-cyano-pyrroles of the general formula (I),

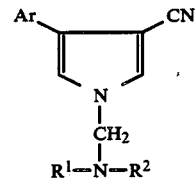

in which
Ar represents optionally substituted phenyl,
$R^1$ represents optionally substituted alkyl, represents alkenyl, alkynyl or cycloalkyl, or represents in each case optionally substituted aralkyl or aryl, and
$R^2$ represents in each case optionally substituted heterocyclylalkyl, heterocyclylalkenyl, heterocyclylalkynyl or heterocyclyl, represents dialkylaminoalkyl, or represents in each case optionally substituted cycloalkylalkyl or phenethyl, are obtained when
(a) 3-aryl-4-cyano-pyrroles of the formula (II),

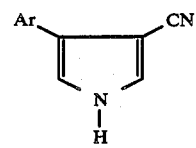

in which
Ar has the abovementioned meaning, are reacted with formaldehyde and amines of the formula (III),

in which
$R^1$ and $R^2$ have the abovementioned meaning, if appropriate in the presence of a diluent and if appropriate in the presence of a reaction auxiliary, or when
(b) 3-aryl-4-cyano-pyrroles of the formula (IV),

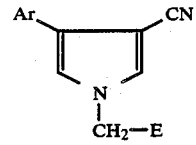

in which
Ar has the abovementioned meaning, and
E represents an electron-withdrawing leaving group, are reacted with amines of the formula (III),

in which
$R^1$ and $R^2$ have the abovementioned meaning, if appropriate in the presence of a diluent and if appropriate in the presence of an acid-binding agent.

Finally, it has been found that the new 1-aminomethyl-3-aryl-4-cyano-pyrroles of the general formula (I) have a good action against pests.

Surprisingly, the 1-aminomethyl-3-aryl-4-cyano-pyrroles of the general formula (I) according to the invention, besides having a better fungicidal activity compared to the previously known dithiocarbamates or sulphenamides from the state of the art, such as, for example, zinc ethylene-1,2-bis-(dithiocarbamate) or manganese ethylene-1,2-bis-(dithiocarbamate) or N,N-dimethyl-N'-phenyl-N'-(fluoro-dichloromethylsulphenyl)-sulphamide, at the same time have a markedly improved crop-plant compatibility compared to the previously known 3-aryl-pyrroles from the state of the art, such as, for example, 4-cyano-3-(2,3-dichlorophenyl)-pyrrole, which are similar compounds chemically and/or regarding their action.

Formula (I) provides a general definition of the 1-aminomethyl-3-aryl-4-cyano-pyrroles according to the invention. Preferred compounds of the formula (I) are those in which Ar represents phenyl which is optionally monosubstituted to polysubstituted by identical or different substituents, suitable substituents being: halogen, in each case straight-chain or branched alkyl, alkoxy, alkylthio, halogenoalkyl, halogenoalkoxy or halogenoalkylthio in each case having 1 to 4 carbon atoms and, if appropriate, 1 to 9 identical or different halogen atoms, $R^1$ represents optionally substituted, straight-chain or branched alkyl having 1 to 6 carbon atoms, suitable substituents being: cyano, cycloalkyl having 3 to 7 carbon atoms, in each case straight-chain or branched alkoxy, alkylcarbonyl, alkoxycarbonyl, alkylaminocarbonyl, dialkylaminocarbonyl, alkylsulphinyl, alkylsulphonyl or dialkylamino in each case having 1 to 6 carbon atoms in the individual alkyl parts; in addition represents in each case straight-chain or branched alkenyl or alkynyl in each case having 3 to 6 carbon atoms, cycloalkyl having 3 to 7 carbon atoms, or phenyl or benzyl which is in each case optionally monosubstituted to polysubstituted in the phenyl part by identical or different substituents, suitable substituents in each case being: halogen, cyano, in each case straight-chain or branched alkyl, alkoxy, halogenoalkyl, halogenoalkoxy, alkylcarbonyl or alkoxycarbonyl in each case having 1 to 6 carbon atoms in the individual alkyl parts and, in the case of the halogenoalkyl or halogenoalkoxy radical, in each case having 1 to 9 identical or different halogen atoms, and represents in each case straight-chain or branched heterocyclylalkyl having 1 to 6 carbon atoms in the alkyl part, heterocyclylalkenyl having 3 to 6 carbon atoms in the alkenyl part, heterocyclylalkynyl having 3 to 6 carbon atoms in the alkynyl part or heterocyclyl, where heterocyclyl in each case represents a 5- to 7-membered heterocyclic ring having 1 to 3 heteroatoms, in particular nitrogen, oxygen or sulphur, which is optionally monosubstituted to polysubstituted by identical or different substituents and where suitable substituents are in each case: halogen, cyano, in each case straight-chain or branched alkyl, alkoxy, halogenoalkyl, halogenoalkoxy, alkylcarbonyl or alkoxycarbonyl in each case having 1 to 6 carbon atoms in the individual alkyl parts and, in the case of the halogenoalkyl or halogenoalkoxy radical, in each case having 1 to 9 identical or different halogen atoms; in addition represents straight-chain or branched dialkylaminoalkyl in each case having 1 to 6 carbon atoms in the individual alkyl parts, furthermore cycloalkylalkyl, having 1 to 6 carbon atoms in the straight-chain or branched alkyl part and 3 to 7 carbon atoms in the cycloalkyl part, which is optionally monosubstituted to polysubstituted in the cycloalkyl part by halogen and/or straight-chain or branched alkyl having 1 to 4 carbon atoms, the substituents being identical or different, or phenylethyl which is optionally monosubstituted to polysubstituted in the phenyl part by cyano, halogen and/or in each case straight-chain or branched alkyl or alkoxy in each case having 1 to 4 carbon atoms, the substituents being identical or different.

Particularly preferred compounds of the formula (I) are those in which

Ar represents optionally monosubstituted, disubstituted or trisubstituted phenyl, the substituents being identical or different and suitable substituents being: fluorine, chlorine, bromine, methyl, ethyl, n- or i-propyl, n-, i-, s- or t-butyl, methoxy, ethoxy, methylthio, trifluoromethyl, trifluoromethoxy or trifluoromethylthio, $R^1$ represents in each case optionally substituted methyl, ethyl or n- or i-propyl, and n-, i- or s-butyl, suitable substituents in each case being: cyano, methoxy, ethoxy, methylcarbonyl, ethylcarbonyl, methoxycarbonyl, ethoxycarbonyl, methylaminocarbonyl, dimethylaminocarbonyl, ethylaminocarbonyl, diethylaminocarbonyl, methylsulphinyl, methylsulphonyl, dimethylamino, diethylamino or dipropylamino, dibutylamino or cyclohexyl; in addition represents allyl, n- or i-butenyl, propargyl, n- or i-butinyl, cyclopentyl, cyclohexyl, cyclopropyl, or benzyl or phenyl which is in each case optionally monosubstituted, disubstituted or trisubstituted in the phenyl part by identical or different substituents, suitable substituents being: fluorine, chlorine, bromine, cyano, methyl, ethyl, n- or i-propyl, n-, i- or s-butyl, methoxy, ethoxy, trifluoromethyl, trifluoromethoxy, acetyl, methoxycarbonyl or ethoxycarbonyl, and $R^2$ represents heterocyclylmethyl, heterocyclylethyl or heterocyclylpropyl which is in each case optionally monosubstituted or disubstituted in the heterocyclyl part by identical or different substituents, one of the following radicals being suitable in each case as the heterocyclyl radical

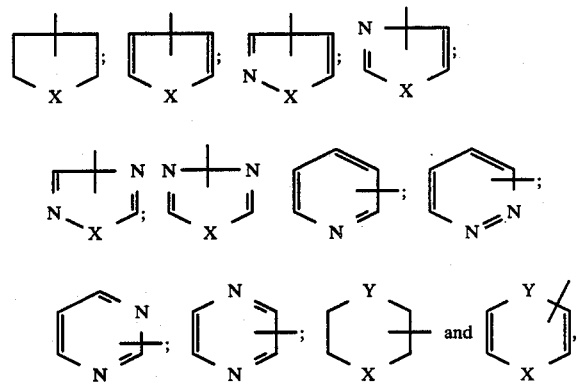

where X in each case represents oxygen, sulphur or an NH group and Y in each case represents oxygen, sulphur, an NH group or a CH$_2$ group, and suitable substituents in each case being: fluorine, chlorine, bromine, cyano, methyl, ethyl, n- or i-propyl, n-, i-, s- or t-butyl, methoxy, ethoxy, trifluoromethyl, trifluoromethoxy, acetyl, methoxycarbonyl or ethoxycarbonyl; in addition represents dimethylaminoethyl, diethylaminoethyl, dimethylaminopropyl, diethylaminopropyl, dipropylaminopropyl, dibutylaminopropyl, dibutylaminobutyl, dibutylaminoethyl, dipropylaminoethyl, dimethylaminobutyl, diethylaminobutyl, dimethylaminopentyl, diethylaminopentyl, represents cyclohexylmethyl or cyclohexylethyl which is in each case optionally monosubstituted, disubstituted or trisubstituted by methyl, ethyl and/or isopropyl, the substituents being identical or different, or represents phenethyl which is optionally monosubstituted, disubstituted or trisubstituted by fluorine, chlorine, bromine, cyano, methyl, ethyl, n- or i-propyl, n-, i-, s- or t-butyl, methoxy, ethoxy, n- or i-propoxy and n-, i-, s- or t-butoxy, the substituents being identical or different.

Very particularly preferred compounds of the formula (I) are those in which

Ar represents phenyl which is disubstituted by chlorine,

R$^1$ represents methyl, ethyl, n- or i-propyl, n-, i- or s-butyl, allyl, propargyl, cyclohexyl, cyclopropyl, cyclopentyl, cyclohexylmethyl, phenyl, benzyl or cyanoethyl, and R$^2$ represents heterocyclylmethyl, heterocyclylethyl or heterocyclylpropyl which is in each case optionally monosubstituted, disubstituted or trisubstituted by chlorine and methyl, the substituents being identical or different and suitable heterocyclyl radicals being:

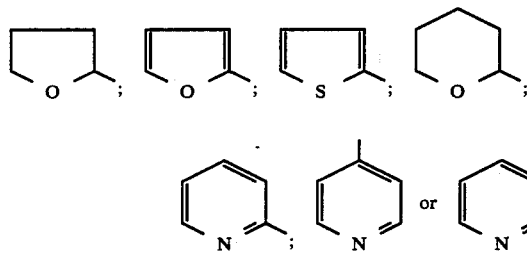

or represents 2-heterocyclylethyl, 2-heterocyclylpropyl or 3-heterocyclylpropyl which is in each case optionally monosubstituted, disubstituted or trisubstituted by methyl and ethyl, the substituents being identical or different and suitable heterocyclyl radicals being:

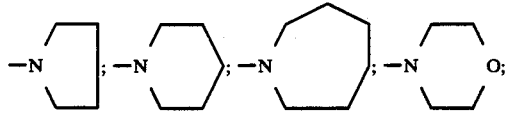

in addition represents diethylaminoethyl, dimethylaminopropyl, diethylaminopropyl, dibutylaminopropyl or diethylaminopentyl, cyclohexylmethyl or phenethyl.

Especially preferred compounds of the formula (I) are those in which

Ar represents 2,3-dichlorophenyl,

R$^1$ represents cyanoethyl and

R$^2$ represents heterocyclylmethyl, heterocyclylethyl or heterocyclylpropyl which is in each case optionally monosubstituted, disubstituted or trisubstituted by chlorine and methyl, the substituents being identical or different and suitable heterocyclyl radicals being:

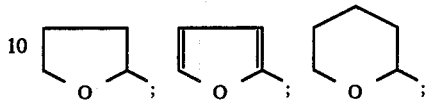

or represents 2-heterocyclylethyl, 2-heterocyclylpropyl or 3-heterocyclylpropyl which is in each case optionally monosubstituted, disubstituted or trisubstituted by methyl and ethyl, the substituents being identical or different and suitable heterocyclyl radicals being:

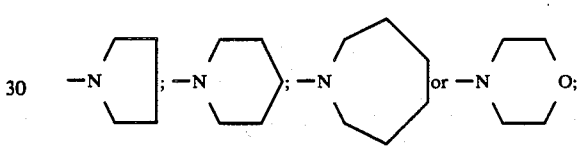

in addition represents diethylaminoethyl, dimethylaminopropyl, diethylaminopropyl, dibutylaminopropyl or diethylaminopentyl, cyclohexylmethyl or phenethyl.

Especially preferred compounds of the formula (I) are additionally those in which Ar represents 2,3-dichlorophenyl, R$^1$ represents methyl, ethyl, n- or i-propyl, n-, i- or s-butyl, allyl, propargyl, cyclopropyl, cyclopentyl, cyclohexyl, cyclohexylmethyl, phenyl, benzyl or cyanoethyl and R$^2$ represents heterocyclylmethyl which is optionally monosubstituted, disubstituted or trisubstituted by chlorine and methyl, the substituents being identical or different and suitable heterocyclyl radicals being:

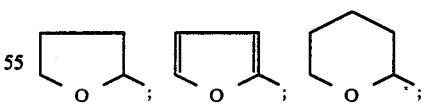

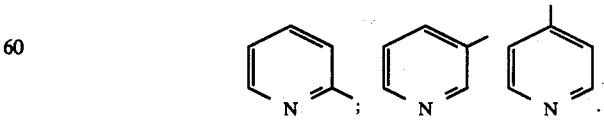

Apart from the compounds mentioned in the preparation examples, the following 1-aminomethyl-3-aryl-4-cyano-pyrroles of the general formula (I) may be mentioned individually:

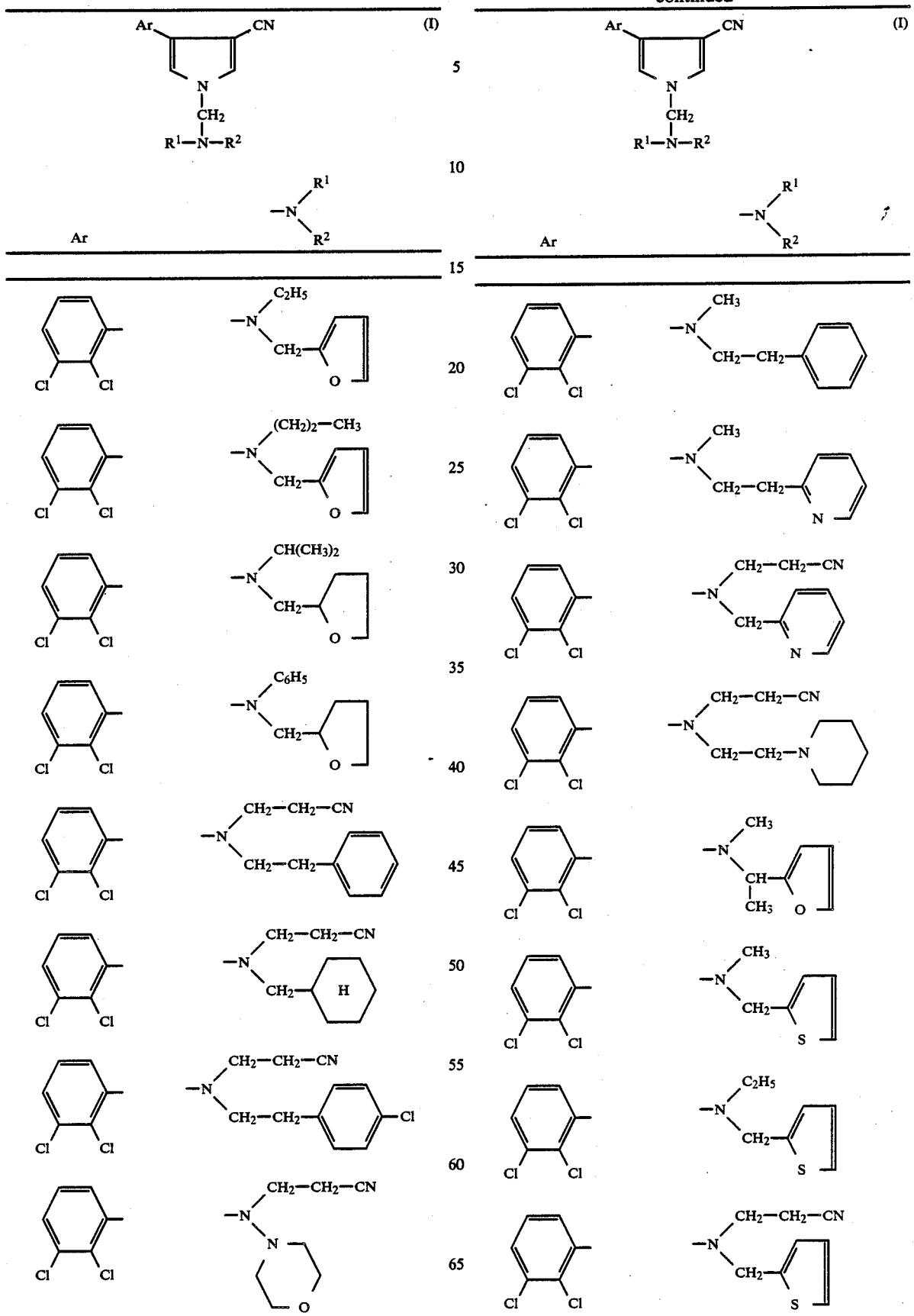

-continued

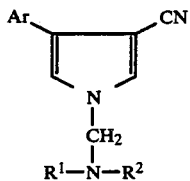  (I)

| Ar | $-N\begin{smallmatrix}R^1\\R^2\end{smallmatrix}$ |
|---|---|
| 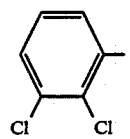 | 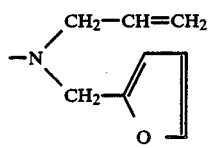 |
| 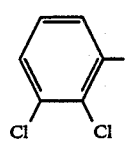 | 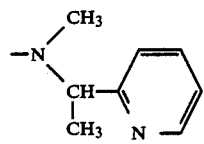 |
| 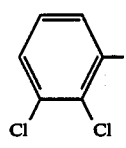 | 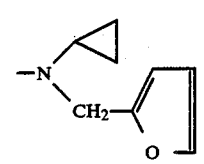 |
| 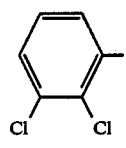 | 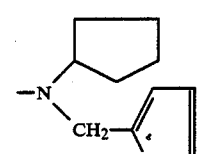 |

If, for example, 4-cyano-3-(2,3-dichlorophenyl)-pyrrole, formaldehyde and N-methyl-N-(2-tetrahydrofurylmethyl)-amine are used as starting materials, the course of the reaction of process (a) according to the invention may be illustrated by the following equation:

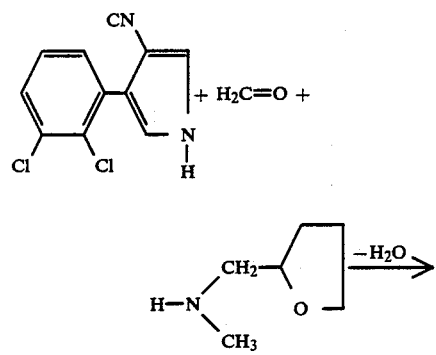

-continued

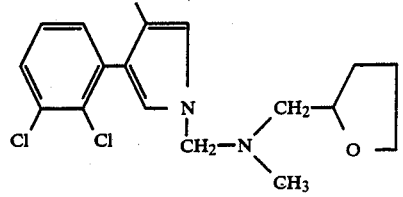

If, for example, 1-chloromethyl-4-cyano-3-(2,3-dichlorophenyl)-pyrrole and N-ethyl-N-(2-furylmethyl)-amine are used as starting materials, the course of the reaction of process (b) according to the invention may be illustrated by the following equation:

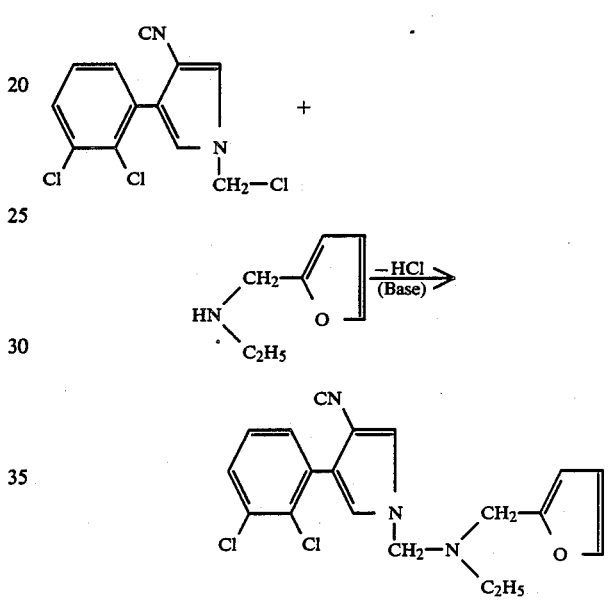

Formula (II) provides a general definition of the 3-aryl-4-cyano-pyrroles which are required as starting materials for carrying out process (a) according to the invention. In this formula (II), Ar preferably represents those radicals which have already been mentioned for this substituent in connection with the description of the substances of the formula (I) according to the invention.

The 3-aryl-4-cyano-pyrroles of the formula (II) are known (cf., for example, EP Nos. 174,910, 182,738 or 133,247).

Formula (IV) provides a general definition of the 3-aryl-4-cyano-pyrroles which are required as starting materials for carrying out process (b) according to the invention. In this formula (IV), Ar preferably represents those radicals which have already been mentioned for this substituent in connection with the description of the substances of the formula (I) according to the invention.

E preferably represents hydroxyl or halogen, in particular chlorine.

The 3-aryl-4-cyano-pyrroles of the formula (IV) are likewise known (cf., for example, EP No. 133,247).

Formula (III) provides a general definition of the amines which are furthermore required as starting materials for carrying out processes (a) and (b) according to the invention. In this formula (III), $R^1$ and $R^2$ preferably represent those radicals which have already been mentioned for these substituents in connection with the description of the substances of the formula (I) according to the invention.

The amines of the formula (III) are generally known compounds of organic chemistry or can be obtained analogously to known processes (cf., for example, GB No. 1,031,916 of 2.6. 1966; Org. Magnet. Res. 7, 488–495 [1975]; Kogyo Kagaku Zasshi 63, 1593–1597 [1960] or CA 60: 10 542 f).

Suitable diluents for carrying out process (a) according to the invention are inert organic solvents or aqueous systems. Protic solvents, for example alcohols, such as methanol, ethanol or propanol, or carboxylic acids, such as formic acid, acetic acid or propionic acid, or mixtures thereof with water, are preferably used. It is also possible to carry out process (a) according to the invention in aprotic solvents. These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides such as dimethyl sulphoxide.

Process (a) according to the invention is carried out, if appropriate, in the presence of a suitable reaction auxiliary. Suitable for this are either catalytic to equimolar amounts of an organic or inorganic acid or corresponding amounts of a suitable base.

Suitable acidic reaction auxiliaries are, in particular, inorganic mineral acids, such as phosphoric acid, sulphuric acid, nitric acid, hydrochloric acid or hydrobromic acid, or organic acids, such as formic acid, acetic acid, propionic acid, methanesulphonic acid, benzenesulphonic acid or toluenesulphonic acid.

Suitable basic reaction auxiliaries are all conventional inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

However, it is also possible to simultaneously employ the amine of the formula (III) used as a reactant as a reaction auxiliary in an appropriate excess.

The reaction temperatures may be varied within a relatively wide range when carrying out process (a) according to the invention. In general, the process is carried out at temperatures between 0° C. and 120° C., preferably at temperatures between 20° C. and 90° C.

In order to carry out process (a) according to the invention, 1.0 to 2.0 moles, preferably 1.0 to 1.5 moles, of amine of the formula (III) and 1.0 to 2.0 moles, preferably 1.0 to 1.5 moles, of formaldehyde are generally employed per mole of 3-aryl-4-cyano-pyrrole of the formula (II). Formaldehyde is employed either in the form of an aqueous solution, as paraformaldehyde or as 1,3,5-trioxane. An aqueous solution is preferably used. The reaction is carried out and the reaction products of the formula (I) are worked up and isolated analogously to known processes (cf. EP No. 133,247).

Suitable diluents for carrying out process (b) according to the invention are inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

Process (b) according to the invention is carried out, if appropriate, in the presence of a suitable acidbinding agent. Suitable as such are all conventional inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

However, it is also possible to simultaneously employ the amine of the formula (III) which is suitable as a reactant as a reaction auxiliary in an appropriate excess.

The reaction temperatures may be varied within a relatively wide range when carrying out process (b) according to the invention. In general, the process is carried out at temperatures between 0° C. and 100° C., preferably at temperatures between 20° C. and 60° C.

In order to carry out process (b) according to the invention, 1.0 to 2.0 moles, preferably 1.0 to 1.5 moles, of amine of the formula (III) and, if appropriate, 1.0 to 2.0 moles, preferably 1.0 to 1.5 moles, of acid-binding agent are generally employed per mole of 3-aryl-4-cyano-pyrrole of the formula (IV). The reaction is carried out and the reaction products of the formula (I) are worked up and isolated analogously to known processes.

The active compounds according to the invention have a strong action against pests and can be employed in practice for combating undesired harmful organisms. The active compounds are suitable, for example, for use as plantprotection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, Pythium ultimum; Phytophthora species, such as, for example, *Phytophthora infestans; Pseudoperonospora* species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosoporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, Alternaria brassicae; Pseudocercosporella species, such as, for example, *Pseudocercosporella herpotrichoides*; and Sclerotinia species, such as, for example, *Sclerotinia sclerotiorum*.

The good toleration, by plants, of the active compounds, at the concentrations required for combating plant diseases, permits treatment of above-ground parts of plants, of vegetative propagation stock and seeds, and of the soil.

The active compounds according to the invention can be used particularly successfully here for combating cereal diseases, such as, for example, against the pathogen of wheat culm rot (*Fusarium culmorum*), for combating rice diseases, such as, for example, against the pathogen of rice spot disease (*Pyricularia oryzae*) or can be employed for combating diseases in fruit and vegetable growing, such as, for example, against the pathogen of gray mold (*Botrytis cinerea*). It should be particularly emphasized here that the active compounds according to the invention, besides a good protective activity, also have systemic properties and are therefore also suitable as seed dressings. A good and broad in vitro activity of the compounds and a good plant compatibility should furthermore be emphasized.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

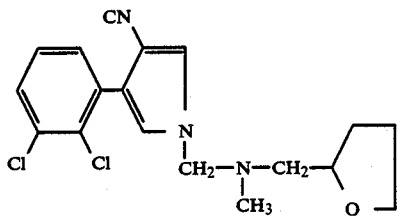

(Process a)

2 ml (0.027 mole) of 37 percent strength aqueous formaldehyde solution and 0.16 ml of acetic acid are added to 4.0 g (0.017 mole) of 4-cyano-3-(2,3-dichlorophenyl)pyrrole (cf. EP No. 133,247) in 14 ml of ethanol. 3.0 g (0.027 mole) of N-methyltetrahydrofurfurylamine (cf. Ital. Pat. No. 510, 118 of 20.1. 1955 or CA 52: 17 287 i) are then added dropwise with stirring, and the mixture is stirred at room temperature for 20 hours after the addition is complete. Work-up is effected by adding 100 ml of ethyl acetate, washing three times with water, drying over sodium sulphate, removing the solvent in vacuo and crystallizing the residue from ether/cyclohexane.

4.0 g (66% of theory) of 4-cyano-3-(2,3-dichlorophenyl)-1-(N-methyl-N-furfuryl-aminomethyl)-pyrrole of melting point 79° C.–80° C. are obtained.

The following 1-aminomethyl-3-aryl-4-cyano-pyrroles of the general formula (I) are obtained in a corresponding fashion and according to the general information on the preparation:

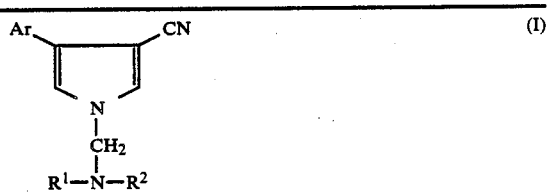

| Ex. No. | Ar | R¹ | R² | Physical properties |
|---|---|---|---|---|
| 2 | 2,3-Cl₂-C₆H₃ | CH₃ | (2-methyl-tetrahydrofuran-2-yl)methyl | $^1$H—NMR*: 4.75–5.0 |
| 3 | 2,3-Cl₂-C₆H₃ | n-C₃H₇ | (tetrahydropyran-2-yl)methyl | m.p. 67–68° C. |
| 4 | 2,3-Cl₂-C₆H₃ | NC—CH₂—CH₂— | (C₂H₅)₂N—(CH₂)₂— | $^1$H—NMR*: 4.9 |
| 5 | 2,3-Cl₂-C₆H₃ | CH₃ | (2,5-dihydrofuran-2-yl)methyl | m.p. 60–61° C. |
| 6 | 2,3-Cl₂-C₆H₃ | n-C₃H₇ | (tetrahydrofuran-2-yl)methyl | $^1$H—NMR*: 4.8–5.1 |
| 7 | 2,3-Cl₂-C₆H₃ | NC—CH₂—CH₂— | (tetrahydrofuran-2-yl)methyl | $^1$H—NMR*: 4.85–5.15 |

-continued

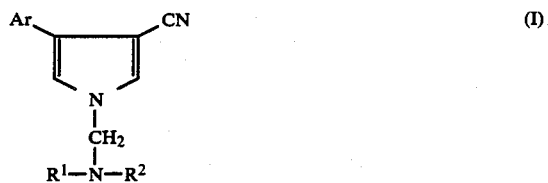

| Ex. No. | Ar | R¹ | R² | Physical properties |
|---|---|---|---|---|
| 8 | 2,3-diCl-C₆H₃- | NC—CH₂—CH₂— | pyridin-2-yl-CH₂—CH₂— | ¹H—NMR*: 4.8 |
| 9 | 2,3-diCl-C₆H₃- | cyclohexyl (H) | furan-2-yl-CH₂— | m.p. 70–71° C. |
| 10 | 2,3-diCl-C₆H₃- | CH₃ | 2,5-dimethylfuran-2-yl-CH₂— | m.p. 68–70° C. |
| 11 | 2,3-diCl-C₆H₃- | NC—CH₂—CH₂— | morpholino-(CH₂)₂— | m.p. 79–80° C. |
| 12 | 2,3-diCl-C₆H₃- | C₂H₅ | tetrahydrofuran-2-yl-CH₂— | ¹H—NMR*: 4.8–5.1 |
| 13 | 2,3-diCl-C₆H₃- | s-C₄H₉ | furan-2-yl-CH₂— | m.p. 40–43° C. |
| 14 | 2,3-diCl-C₆H₃- | CH₃ | pyridin-2-yl-CH₂— | m.p. 65–66° C. |
| 15 | 2,3-diCl-C₆H₃- | i-C₄H₉ | tetrahydrofuran-2-yl-CH₂— | m.p. 64–65° C. |
| 16 | 2,3-diCl-C₆H₃- | NC—CH₂—CH₂— | morpholino-(CH₂)₃— | m.p. 62–63° C. |

-continued

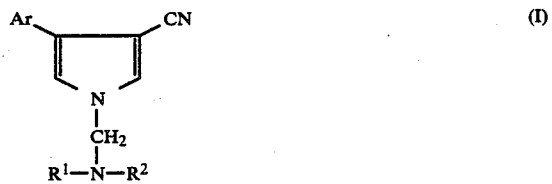
(I)

| Ex. No. | Ar | R¹ | R² | Physical properties |
|---|---|---|---|---|
| 17 | 2,3-Cl₂-C₆H₃ | i-C₃H₇ | furan-2-yl-CH₂— | ¹H—NMR*: 4.65 |
| 18 | 2,3-Cl₂-C₆H₃ | CH₃ | 2,5-dimethyl-tetrahydrofuran-CH₂— | ¹H—NMR*: 4.8–5.0 |
| 19 | 2,3-Cl₂-C₆H₃ | cyclohexyl | tetrahydropyran-2-yl-CH₂— | ¹H—NMR*: 4.8–5.0 |
| 20 | 2,3-Cl₂-C₆H₃ | NC—CH₂—CH₂— | (CH₃)₂N—(CH₂)₃— | ¹H—NMR*: 4.8 |
| 21 | 2,3-Cl₂-C₆H₃ | NC—CH₂—CH₂— | (C₂H₅)₂N—(CH₂)₃— | ¹H—NMR*: 4.85 |
| 22 | 2,3-Cl₂-C₆H₃ | NC—CH₂—CH₂— | (C₂H₅)₂N—(CH₂)₃—CH(CH₃)— | ¹H—NMR*: 4.7–4.9 |
| 23 | 2,3-Cl₂-C₆H₃ | NC—CH₂—CH₂— | furan-2-yl-CH₂— | ¹H—NMR*: 4.8 |
| 24 | 2,3-Cl₂-C₆H₃ | cyclohexyl-CH₂— | tetrahydrofuran-2-yl-CH₂— | m.p. 84–85° C. |
| 25 | 2,3-Cl₂-C₆H₃ | NC—CH₂—CH₂— | (n-C₄H₉)₂N—(CH₂)₃— | ¹H—NMR*: 4.8 |

-continued

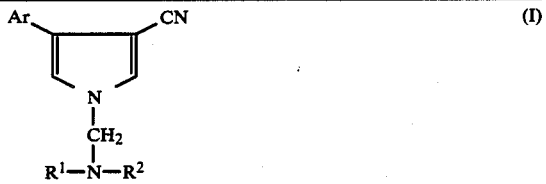

| Ex. No. | Ar | R¹ | R² | Physical properties |
|---|---|---|---|---|
| 26 | 2,3-Cl₂-C₆H₃- | NC—CH₂—CH₂— | 2-CH₃-piperidin-1-yl-(CH₂)₃— | m.p. 57–59° C. |
| 27 | 2,3-Cl₂-C₆H₃- | CH₃ | pyridin-4-yl-CH₂— | ¹H—NMR*: 4.8 |
| 28 | 2,3-Cl₂-C₆H₃- | CH₃ | pyridin-3-yl-CH₂— | ¹H—NMR*: 4.8 |
| 29 | 2,3-Cl₂-C₆H₃- | C₂H₅ | furan-2-yl-CH₂— | ¹H—NMR*: 4.75 |
| 30 | 2,3-Cl₂-C₆H₃- | C₃H₇-n | furan-2-yl-CH₂— | ¹H—NMR*: 4.70 |
| 31 | 2,3-Cl₂-C₆H₃- | NC—CH₂CH₂— | C₆H₅—CH₂CH₂— | m.p. 69–70° C. |
| 32 | 2,3-Cl₂-C₆H₃- | NC—CH₂CH₂— | cyclohexyl-CH₂— | ¹H—NMR⁺: 4.80 |
| 33 | 4-Cl-C₆H₄- | CH₃ | furan-2-yl-CH₂— | ¹H—NMR*: 4.70 |
| 34 | 2,3-Cl₂-C₆H₃- | C₃H₇-n | thien-2-yl-CH₂— | m.p. 86–87° C. |
| 35 | 2-Cl-3-CH₃-C₆H₃- | CH₃ | furan-2-yl-CH₂— | ¹H—NMR*: 4.70 |

-continued $$\text{(I)}$$

| Ex. No. | Ar | $R^1$ | $R^2$ | Physical properties |
|---|---|---|---|---|
| 36 | 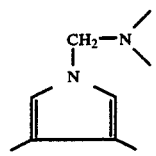 | H—⬡— | 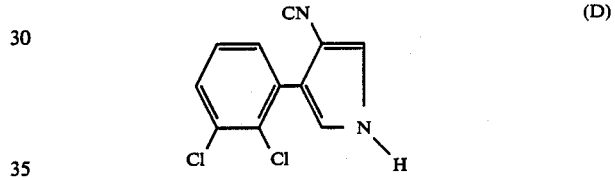 (furan-CH₂—) | $^1$H—NMR*: 4.80 |

*The $^1$H—NMR spectra were recorded in CDCl$_3$ using tetramethylsilane (TMS) as the internal standard. The chemical shift of the group is given as the δ-value in ppm.

USE EXAMPLES

In the following use examples, the compounds shown below were employed as comparison substances:

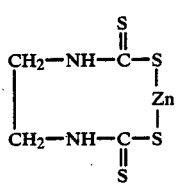 (A)

zinc ethylene-1,2-bis-(dithiocarbamate);

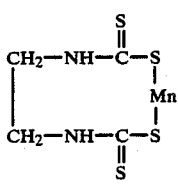 (B)

manganese ethylene-1,2-bis-(dithiocarbamate);

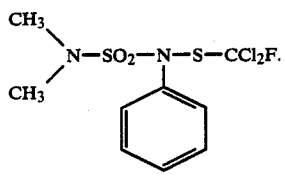 (C)

N,N-dimethyl-N'-(fluorodichloromethylsulphenyl)sulphamide and (D)

4-cyano-3-(2,3-dichlorophenyl)-pyrrole (known from EP No. 174,910).

EXAMPLE A

*Fusarium culmorum* test (wheat)/seed treatment

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 batches of 100 grains of the wheat are sown 1 cm deep in standard soil and are cultivated in a greenhouse at a temperature of about 18° C. in seedboxes which are exposed to light for 15 hours daily.

About 3 weeks after sowing, the plants are evaluated for symptoms.

In this test, for example, the compounds according to the following preparation examples exhibit a clearly superior activity compared to the prior art: 2 and 6.

EXAMPLE B

Botrytis test (bean)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

In this test, for example, the compounds according to the following preparation examples exhibit a clearly superior activity compared to the prior art: 1, 2, 3, 5, 7 and 9.

EXAMPLE C

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, for example, the compounds according to the following preparation examples exhibit a clearly superior activity compared to the prior art: 1, 4, 7, 8 and 9.

EXAMPLE D

Plant tolerance test
Test plant: vines
Duration of the test: 6 days
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

Young plants are sprayed with this preparation of active compound until dripping wet and are placed in a greenhouse at about 20° C.

The plants are evaluated for damage, such as impairment of growth, discoloration and necroses. After the specified periods of time, the degree of damage to the plants is determined.

In this test, for example, the compounds according to the following preparation examples exhibit clearly superior plant compatibility to the prior art: 5 and 9.

It is understood that the specification and examples are illustrative but not limitative of the present invention and that other embodiments within the spirit and scope of the invention will suggest themselves to those skilled in the art.

We claim:

1. A 1-aminomethyl-3-aryl-4-cyanopyrrole of the formula

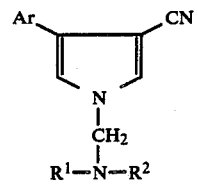

in which

Ar represents optionally substituted phenyl, $R^1$ represents optionally substituted alkyl, represents alkenyl, alkynyl or cycloalkyl, or represents in each case optionally substituted aralkyl or aryl, and $R^2$ represents in each case optionally substituted heterocyclylalkyl, heterocyclylalkenyl, heterocyclylalkynyl or heterocyclyl, where heterocyclyl in each case represents a morpholine or thiomorpholine radical.

2. A 1-aminomethyl-3-aryl-4-cyano-pyrrole according to claim 1, in which

Ar represents phenyl which is optionally substituted by halogen, or by alkyl, alkoxy, alkylthio, halogenoalkyl, halogenoalkoxy or halogenoalkylthio in each case having 1 to 4 carbon atoms and, if appropriate, 1 to 9 identical or different halogen atoms, $R^1$ represents alkyl having 1 to 6 carbon atoms and optionally substituted by cyano, cycloalkyl having 3 to 7 carbon atoms, alkoxy, alkylcarbonyl, alkoxycarbonyl, alkylaminocarbonyl, dialkylaminocarbonyl, alkylsulphinyl, alkylsulphonyl or dialkylamino in each case having 1 to 6 carbon atoms in the individual alkyl parts; in addition represents alkenyl or alkynyl in each case having 3 to 6 carbon atoms, cycloalkyl having 3 to 7 carbon atoms, or phenyl or benzyl which is in each case optionally substituted in the phenyl part by halogen, cyano, alkyl, alkoxy, halogenoalkyl, halogenoalkoxy, alkylcarbonyl or alkoxycarbonyl in each case having 1 to 6 carbon atoms in the individual alkyl parts and, in the case of the halogenoalkyl or halogenoalkoxy radical, in each case having 1 to 9 identical or different halogen atoms, and $R^2$ represents heterocyclylalkyl having 1 to 6 carbon atoms in the alkyl part, heterocyclylalkenyl having 3 to 6 carbon atoms in the alkenyl part, heterocyclylalkynyl having 3 to 6 carbon atoms in the alkynyl part or heterocyclyl, where heterocyclyl in each case represents a morpholine or thiomorpholine, which is optionally substituted by halogen, cyano, alkyl, alkoxy, halogenoalkyl, halogenoalkoxy, alkylcarbonyl or alkoxycarbonyl in each case having 1 to 6 carbon atoms in the individual alkyl parts and, in the case of the halogenoalkyl or halogenoalkoxy radical, in each case having 1 to 9 identical or different halogen atoms in the individual alkyl parts, furthermore cycloalkylalkyl, having 1 to 6 carbon atoms in the alkyl part and 3 to 7 carbon atoms in the cycloalkyl part, which is optionally substituted in the cycloalkyl part by halogen and straight-chain or branched alkyl having 1 to 4 carbon atoms, or phenylethyl which is optionally substituted in the phenyl part by cyano, halogen, or alkyl or alkoxy in each case having 1 to 4 carbon atoms.

3. A 1-aminomethyl-3-aryl-4-cyano-pyrrole according to claim 1,
in which
Ar represents phenyl optionally mono- or independently di or tri-substituted by fluorine, chlorine, bromine, methyl, ethyl, n- or i-propyl, n-, i-, s- or t-butyl, methoxy, ethoxy, methylthio, trifluoromethyl, trifluoromethoxy or trifluoromethylthio, $R^1$ represents methyl, ethyl, n- or i-propyl, or n-, i- or s-butyl, each optionally substituted by cyano, methoxy, ethoxy, methylcarbonyl, ethylcarbonyl, methoxycarbonyl, ethoxycarbonyl, methylaminocarbonyl, dimethylaminocarbonyl, ethylaminocarbonyl, diethylaminocarbonyl, methylsulphinyl, methylsulphonyl, dimethylamino, diethylamino or dipropylamino, dibutylamino or cyclohexyl; or represents allyl, n- or i-butenyl, propargyl, n- or i-butinyl, cyclopentyl, cyclohexyl, cyclopropyl, or benzyl or phenyl which is in each case optionally mono- or independently di- or tri-substituted in the phenyl part by fluorine, chlorine, bromine, cyano, methyl, ethyl, n- or i-propyl, n-, or s-butyl, methoxy, ethoxy, trifluoromethyl, trifluoromethoxy, acetyl, methoxycarbonyl or ethoxycarbonyl, and $R^2$ represents heterocyclylmethyl, heterocyclylethyl or heterocyclylpropyl which is in each case optionally monosubstituted or disubstituted in the heterocyclyl part by identical or different substituents, the heterocyclyl radical being selected from the group consisting of morpholine and thiomorpholine the optional substituents being selected from the group consisting of fluorine, chlorine, bromine, cyano, methyl, ethyl, n- or i-propyl, n-, i-, s- or t-butyl, methoxy, ethoxy, trifluoromethyl, trifluoromethoxy, acetyl, methoxycarbonyl and ethoxycarbonyl.

4. A 1-aminomethyl-3-aryl-4-cyano-pyrrole according to claim 1,
in which
Ar represents phenyl which is disubstituted by chlorine, $R^1$ represents methyl, ethyl, n- or i-propyl, n-, i- or s-butyl, allyl, propargyl, cyclohexyl, cyclopropyl, cyclopentyl, cyclohexylmethyl, phenyl, benzyl or cyanoethyl, and $R^2$ represents heterocyclylmethyl, heterocyclylethyl or heterocyclylpropyl which is in each case optionally mono- or independently di- or trisubstituted by chlorine or methyl, the heterocyclyl radicals being selected from the group consisting of morpholine and thiomorpholine.

5. A 1-aminomethyl-3-aryl-4-cyano-pyrrole according to claim 1,
in which
Ar represents 2,3-dichlorophenyl,
$R^1$ represents cyanoethyl and
$R^2$ represents heterocyclymethyl, heterocyclylethyl or heterocyclylpropyl which is in each case optionally mono- or independently di- or trisubstituted by chlorine or methyl, the heterocyclyl radicals being selected from the group consisting of morpholine and thiomorpholine.

6. A 1-aminomethyl-3-aryl-4-cyano-pyrrole according to claim 1,
in which
Ar represents 2,3-dichlorophenyl,
$R^1$ represents methyl, ethyl, n- or i-propyl, n-, i- or s-butyl, allyl, propargyl, cyclopropyl, cyclopentyl, cyclohexyl, cyclohexylmethyl, phenyl, benzyl or cyanoethyl and
$R^2$ represents heterocyclylmethyl which is optionally mono- or independently di- or trisubstituted by chlorine or methyl, the heterocyclyl radicals being selected from the group consisting of morpholine and thiomorpholine.

7. A compound according to claim 1, wherein such compound is 4-cyano-3-(2,3-dichlorophenyl)-1-(N-cyanoethyl-N-morpholin-4-yl-ethyl-aminomethyl)-pyrrole of the formula

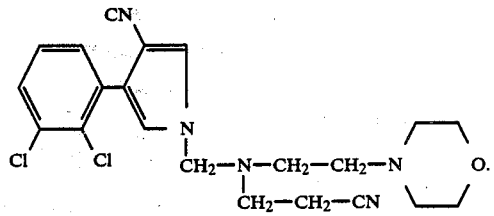

8. A compound according to claim 1, wherein such compound is 4-cyano-3-(2,3-dichlorophenyl)-1-(N-cyanoethyl-N-morpholin-4-yl-propyl-amino-methyl)-pyrrole of the formula

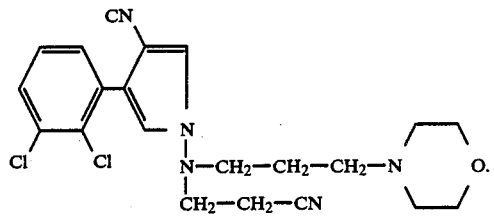

9. The method according to claim 1, wherein such compound is
4-cyano-3-(2,3-dichlorophenyl)-1-(N-cyanoethyl-N-morpholin-4-yl-ethyl-aminomethyl)-pyrrole or 4-cyano-3-(2,3-dichlorophenyl)-1-(N-cyanoethyl-N-morpholin-4-yl-propyl-amino-methyl)-pyrrole.

10. A fungicidal composition comprising a fungicidally effective amount of a 1-aminomethyl-3-aryl-4-cyano-pyrrole according to claim 1 and a diluent.

11. A method of combating fungi which comprises applying to such fungi or to a fungus habitat a fungicidally effective amount of a 1-aminomethyl-3-aryl-4-cyano-pyrrole according to claim 1.

* * * * *

UNITED STATES PATENT AND TRADEMARK OFFICE
CERTIFICATE OF CORRECTION

PATENT NO. : 4,957,919

DATED : September 18, 1990

INVENTOR(S) : Wollweber et al.

It is certified that error appears in the above-identified patent and that said Letters Patent is hereby corrected as shown below:

Col. 26, lines 52-53  After " thiomorpholine " insert -- radical --

Signed and Sealed this

Twenty-fifth Day of August, 1992

*Attest:*

DOUGLAS B. COMER

*Attesting Officer*  Acting Commissioner of Patents and Trademarks

UNITED STATES PATENT AND TRADEMARK OFFICE
CERTIFICATE OF CORRECTION

PATENT NO. : 4,957,919

DATED : September 18, 1990

INVENTOR(S) : Wollweber et al.

It is certified that error appears in the above-identified patent and that said Letters Patent is hereby corrected as shown below:

Col. 26, lines 59-67   After " atoms " delete " in the individual alkyl parts, furthermore cycloalkylalkyl, having 1 to 6 carbon atoms in the alkyl part and 3 to 7 carbon atoms in the cycloalkyl part, which is optionally substituted in the cycloalkyl part by halogen and straight-chain or branched alkyl having 1 to 4 carbon atoms, or phenylethyl which is optionally substituted in the phenyl part by cyano, halogen, or alkyl or alkoxy in each case having 1 to 4 carbon atoms "

Signed and Sealed this

Seventeenth Day of August, 1993

Attest:

BRUCE LEHMAN

Attesting Officer

Commissioner of Patents and Trademarks